United States Patent [19]

Konobe et al.

[11] 4,071,618

[45] Jan. 31, 1978

[54] PROCESS FOR PREPARING VIRUS DISEASE LIVE VACCINES

[75] Inventors: Takeo Konobe; Tetsuo Onoda; Koichi Ono, all of Kanonji, Japan

[73] Assignee: Research Foundation for Microbial Diseases of Osaka University, Osaka, Japan

[21] Appl. No.: 702,398

[22] Filed: July 6, 1976

Related U.S. Application Data

[63] Continuation of Ser. No. 502,633, Sept. 3, 1974, abandoned, which is a continuation of Ser. No. 309,692, Nov. 27, 1972, abandoned, which is a continuation of Ser. No. 313,539, April 5, 1971, abandoned.

[51] Int. Cl.$^2$ .................. A61K 39/12; C12B 3/00; C12K 9/00
[52] U.S. Cl. ...................... 424/89; 195/1.1; 195/1.3
[58] Field of Search .................. 195/1.3, 1.1; 424/89

[56] References Cited

U.S. PATENT DOCUMENTS 3,674,861   7/1972   Churchill ........................ 195/1.3

OTHER PUBLICATIONS

Veronin et al., Vop. Virus, vol. 13, (1968) pp. 345–352.

*Primary Examiner*—Sam Rosen
*Attorney, Agent, or Firm*—Armstrong, Nikaido & Marmelstein

[57] ABSTRACT

Process for preparing a virus disease live vaccine by employing culture of a quail embryonated egg or tissue culture of a quail embryo fibroblast for cultivation of the virus. The vaccine obtained according to the present invention is effective for immunization of animals and humans against the virus disease. The vaccine is avirulent, scarcely subject to induction of unfavorable factors accompanying the present tissue used for isolation of the virus therefrom, and economically producible.

10 Claims, No Drawings

PROCESS FOR PREPARING VIRUS DISEASE LIVE VACCINES

The present application is a continuation of prior application Ser. No. 502,633 filed Sept. 3, 1974, and now abandoned. Application Ser. No. 502,633 is a continuation of application Ser. No. 309,692 filed Nov. 27, 1972, and now abandoned. Application Ser. No. 309,692, in turn, is a continuation of original application Ser. No. 313,539, filed Apr. 5, 1971, and which is also abandoned.

This invention relates to the preparation of a vaccine for animals and humans, and more particularly to a process for the preparation of a live vaccine for immunization of animals and humans against virus diseases by employing tissue culture of a quail embryo fibroblast or a quail embryonated egg.

Beginning from the investigation by Harrison, the technique of tissue culture has been developed by A. Carrel, A. Fisher, G. Levi, etc. in the 1910 to 1920's. Since Enders et al succeeded in the propagation of polic virus by the technique of tissue culture, this technique has been utilized for the propagation of various viruses. And nowadays, the tissue culture method is widely and advantageously used for the preparation of virus vaccines.

With the tissue culture conventionally employed, there is such serious problem that, according to the kind of tissue supplying animal used, the unfavorable factors accompanying the parent cells often causes the culture cells to be stained therewith, leading to the induction of such favorable factors to the produced vaccines. In general, it is very difficult to previously detect non-manifestative infection of the tissue supplying animal with such unfavorable factors. For example, various simian viruses are often detected from the apparently healthy monkeys, leading to difficulty in the preparation of polio live vaccine. In addition, it was also reported that Newcastle virus was detected in the tissue cultures of the apparently normal chick embryo fibroblasts. It was also reported that the use of chick kidney as a medium for culturing Marek's disease virus is inevitably accompanied by danger of unfavorable induction of leukemia virus of wild chicken to the produced Marek's disease vaccine.

For the reason as stated above, careful attention should be given to danger of induction of the accompanying unfavorable factors, in case of employing the tissue culture method in the preparation of vaccine. Moreover, the tissue culture methods conventionally employed have various disadvantages that the availability of materials is restricted in regard to quantity, and that they require complicated operation and assay.

As a result of our extensive and intensive investigation to overcome such drawbacks as unavoidable in the conventional tissue culture, it has been found that the culture of a quail embryonated egg or the tissue culture of a quail embryo fibroblast is extremely suitable for cultivation of viruses for producing virus disease vaccines.

It is one object of the present invention to provide a process for the preparation of a virus disease live vaccine which is very effective for immunization of animals and humans against the virus disease.

It is another object of the present invention to provide a process for the preparation of a virus disease live vaccine which is extremely avirulent, ensuring safety of animals and humans inoculated therewith.

It is a further object of the present invention to provide a process for the preparation of a virus disease live vaccine in which unfavorable factors are scarcely induced.

It is a still further object of the present invention to provide a process of the character described, which is simple in operation and economical, thus enabling the production of virus disease vaccine to be economical.

Essentially, according to the present invention, there is provided a process for the preparation of a virus disease vaccine which comprises employing a quail embryonated egg or tissue culture of a quail embryo fibroblast for cultivation the virus.

By employing, as a culture medium for viruses, culture of a quail embryonated egg or tissue culture of a quail embryo fibroblast, not only the high quality virus live vaccine can be obtained but also the problems of poor availability of materials and complicacy of operation are advantageously eliminated.

The advantages which the use of a quail embryonated egg (QEE) or a tissue culture of quail embryo fibroblast (QEF) has are as follows.

1. Considerable kinds of viruses have an affinity to QEE and a tissue culture of QEF can grow and propagate to an extent sufficient to produce vaccine.

2. QEE and a tissue culture of QEF are scarcely accompanied by danger of induction thereinto chicken leukemia virus, as opposed to a chick embryonated egg.

3. QEE and a tissue culture of QEF are readily available at low cost.

4. From the view point of tissue culture, the number of cells harvested from one embryo of a quail embryonated egg is approximately the same with that of a chick embryonated egg. Moreover, since a quail is smaller than a chicken, large number of quails can be bred in a given area, as compared with chickens. Breeding control with respect to SPF is readily conducted.

5. Particulary for the preparation of chicken disease vaccine, superior vaccines having high safety can be produced by employing quails which rarely have therein microorganisms etiological to chickens.

The isolation of disease viruses from the infected materials, the adaptation, growth and propagation the isolated viruses may be conducted in accordance with the ordinary methods well known to those skilled in the art.

Examples of virus diseases include rubella, measles, mumps, influenza A, influenza B, distemper, vaccinia, Newcastle disease, Japanese encephalitis, dengue fever, rabies, Marek's disease and the like.

As described, according to the present invention, superior quality viral diseases live vaccines can be prepared simply and economically. Moreover, it is particularly advantageous that live vaccines according to the present invention has scarcely danger of induction therein of unfavorable factors from the parent tissue.

The present invention is illustrated, by way of example only, with reference to the following examples.

REFERENCE EXAMPLE 1

The chickens and quails bred according to the ordinary method are examined with respect to infection with chicken leukemia virus (hereinafter referred to as "RIF") to which careful attention should be given especially when live vaccines are intended. The examination was conducted in accordance with the method by Rubin (Proc. Nat. Acad. Sci. 46 1105, 1960) and the method by Sarma et al (Virology, 23 313, 1964). The results are shown in Table 1.

Table 1

|  | Chicken | | Quail | |
| --- | --- | --- | --- | --- |
|  | Number of test chickens | Number of chickens showing positive reaction | Number of test quails | Number of quails showing positive reaction |
| Anti-RIF of parent bird | 53 | 52 | 135 | 0 |
| Detection of RIF from embryo | 83 | 3 | 163 | 0 |
| Detection of RIF from parent bird | 67 | 2 | 85 | 0 |

As clearly understood from Table 1, most of the adult chickens were proved to have anti-RIF, which showed the fact that most of chickens were infected with RIF. By contrast, all the test adult quails were proved to have not anti-RIF. The examination of bloods and visceral organs of embryo and adult birds with respect to detection of RIF, no RIF was detected from all the test adult quails. From the results, it can be fairly concluded that the probability of natural infection of quails with RIF is extremely low.

REFERENCE EXAMPLE 2

A chick embryonated egg and a quail embryonated egg were respectively treated in accordance with the ordinary method, to disperse the cells thereof. Then, the number of cells per one embryo was measured and shown in Table 2.

Table 2

| Kind of embryo | Number of cells |
| --- | --- |
| Chicken | $8.0 \times 10^7 - 8.9 \times 10^7$ |
| Quail | $7.8 \times 10^7 - 8.8 \times 10^7$ |

As apparent from Table 2, with regard to the numbers of the cells obtained through tissue culture of embryo, chicken and quail are approximately the same with each other.

REFERENCE EXAMPLE 3

Isolation of virus of Marek's disease (hereinafter referred to simply as "MD")

As a material for isolating therefrom wild MD virus, there was employed whole blood or tumor tissues of chicken infected with MD. According to the ordinary procedure, the tumor tissue was treated with trypsin and the cells thereof were dispersed. Then, they were suspended in Eagle's culture solution.

On the other hand, 7 to 15-day-old quail embryo was treated according to the ordinary procedure, to disperse the cells thereof. The thus obtained fibroblasts were plated at $2.4 \times 10^6$ cells per 6cm-diametered dish. On the next day, the fibroblasts on dishes each were inoculated with 1 ml. of the above-mentioned whole blood or tumor tissue suspension, whereupn they were cultivated in an incubator (containing carbon dioxide gas in an amount of 5%) at 37° C. for 4 – 7 days. The results are summarized in Table 1 in which "+" and "–" show detection and non-detection of the MD virus isolated in and adapted to each fibroblast culture, respectively.

For comparative purpose, the results respectively obtained by using chick kidney, duck embryo and turkey embryo as culture medium are also shown.

Table 3

| Infected chicken (No. of test sample) | Material used | DEC [1] | | QEC [2] | | CK [3] | | TEC [4] | |
| --- | --- | --- | --- | --- | --- | --- | --- | --- | --- |
|  |  | CPE [4] | IF [5] | CPE | IF | CPE | IF | CPE | IF |
| 13 | Lever | + | + | – | – | + | + |  |  |
|  | Spleen | + | + | – | – | + | + |  |  |
|  | Kidney | + | + | + | + | + | + |  |  |
|  | Blood | + | + | + | + | + | + | + | + |
| 22 | Lever | + | + | – | – | + | + |  |  |
|  | Spleen | + | + | – | – | + | + |  |  |
|  | Kidney | + | + | – | – | + | + |  |  |
|  | Blood | + | + | + | + | + | + | + | + |
| 23 | Lever | + | + | – | – | + | + |  |  |
|  | Spleen | + | + | – | – | + | + |  |  |
|  | Kidney | + | + | – | – | + | + |  |  |
|  | Blood | – | – | – | – | – | – | + | + |
| 76 | Lever | + | + | – | – | + | + |  |  |
|  | Spleen | + | + | – | – | + | + |  |  |
|  | Kidney | + | + | – | – | + | + |  |  |
|  | Blood | + | + | – | – | + | + | + | + |
| 105 | Lever | + | + | + | + | + | + |  |  |
|  | Spleen | + | + | – | – | + | + |  |  |
|  | Kidney | + | + | – | – | + | + |  |  |
|  | Blood | + | + | + | + | + | + | + | + |

Note:
[1] Duck embryo fibroblast culture
[2] Quail embryo fibroblast culture
[3] Chick kidney culture
[4] Turkey embryo fibroblast culture
[5] Cytopathic effect
[6] Immuno-fluorescence technique As apparent from Table 1, MD virus was detected in DEC, QEC and TEC as well as CK. It should be noted that MD virus could be isolated through QEC, and TEC also. From the other view point, it was noted that MD virus was separated from whole blood of affected chicken in a high proportion of 4/5, and from liver, kidney and spleen each in a proportion of 5/5.

The thus isolated viruses each have an affinity to cells of duck, quail and chick embryoes. It was also observed that these viruses can be further grown upon successive cultivation.

As noted in Table 1, whether or not the embryo fibroblast used was infected with MD virus was determined by means of a cytopathic effect and immunofluorescence technique. The obtained result was further examined by means of an electron microscope.

EXAMPLE 1

The quail, duck and chick embryo fibroblasts prepared in the same manner as described in Reference Example 3, each were suspended in Eagle's culture solution in a concentration of about $5 \times 10^5$ cells per ml., and then poured, by 100ml., in Roux's culture bottles. They were allowed to stand in an incubator at 37° C. for 1 day. Whereupon the fibroblast cultures as prepared above, each were inoculated with BIKEN C strain of MD virus. Volume of inoculum per bottle was 1 ml. One day after the inoculation, the culture solution was removed, and then the cells attached to the bottle wall was washed with Hanks' solution, whereupon Eagle's culture solution was poured thereinto. Cultivation was further continued at 37° C. for 4 to 7 days until alteration of the cells progressed to an extent of 40 to 45% based on the total cells. Then, cultivating operation was terminated. After termination of cultivation, the cells were taken to obtain infected embryo fibroblast cultures, which were suspended in Eagle's culture solution in a concentration of $5 \times 10^6$ cells per ml. to obtain an infected culture suspension, and then stored upon addition of a suitable stabilizer, for example glycerin.

Examination was done on each of the thus obtained infected embryo fibroblast cultures with respect to various properties, in accordance with the draft U.S. Standards for Approval of Vaccine to ensure the adaptability as vaccine. Then, they were formulated to commercial MD live vaccine.

EXAMPLE 2

MD virus isolated through DEC, for example BIKEN Q strain of MD virus was subjected to 6-passage, 36-passage and 46-passage successive cultivation using only QEC. On the other hand, BIKEN C strain of MD virus was subjected to 12-passage successive cultivation using DEC, and 24-passage, 27-passage, 46 passage or 72-passage successive cultivation using QEC.

The thus obtained two cultures each were treated in the same manner as described in Example 1 to obtain an infected culture suspension. The obtained infected culture suspensions were stored on addition of a suitable stabliizer, for example glycerin, whereupon its ability of immunization of chicken against MD was examined.

The vaccines obtained according to the abovementioned experiments had a sufficient activity of immunization on storage at 4° C. for 1 week, and even on storage at very low temperature, for example — 70° C. for 2 months.

Table 2 shows the effects of the vaccines obtained.

Table 4

| Experiment group | Number of chick used | Age of chick inoculated with virulent strain of MD virus (day-old) | Inoculation of vaccine: Successive cultivation 2) | Inoculation of vaccine: Age of chick inoculated with the vaccine (day-old) | Age of test chick when contacted with offected chick (day-old) 3) | Number of Mortality due to MD 4) | Rate of Mortality due to MD |
|---|---|---|---|---|---|---|---|
| $A_1$(Control) | 20 | 1 | — | — | — | 14 | 14/20 (70%) |
| $A_2$ | 20 | — | BIKEN C strain DEC 12 →QEC 46 | 1 | — | 0 | 0/20 |
| $A_3$ | 19 | — | BIKEN C strain DEC 12 →QEC 72 | 1 | 48 | 0 | 0/19 |
| $B_1$(Control) | 38 | 1 | — | — | — | 15 | 15/38 (39%) |
| $B_2$ | 20 | — | BIKEN Q strain QEC 6 | 1 | — | 6 | 7/20 (35%) |
| $B_3$ | 50 | — | BIKEN Q strain QEC 36 | 1 | — | 2 | 2/50 (4%) |
| $B_4$ | 50 | — | BIKEN Q strain QEC 46 | 1 | 52 | 0 | 0/50 |
| $B_5$ | 50 | — | BIKEN C strain DEC 12 →QEC 24 | 18 | — | 0 | 0/50 |
| $B_6$ | 48 | — | BIKEN C strain DEC 12 →QEC 27 | 1 | 49 | 1 | 1/48 (2%) |

(Note)
A: White leghorn
B: De Carb 161
The inoculations (0.2 ml. each) were effected to the abdominal cavity. The period of time of observation was limited to 26-week-old.
1) The vilurent strain of MD virus is a strain successively cultivated following of inoculation of chick abdominal cavity with blood of chick infected with MD.
2) The "BIKEN C strain" and "BIKEN E strain" are the names of strains of MD viruses. Their infectivities are each $10^{4-5/ml}$ expressed in terms of plaqueforming unit (PFU). The number attached after the abbreviations DEC and QEC shows the number of succession of cultivation.
3) Test chicks were bred together with several chicks recognized to be affected with MD in the same poultry house.
4) The affected and dead chicks were all subjected to autopsy and examined, and they are all proved to be of MD in view of pathology.

As apparent from Table 2, the vaccine obtained on high passage (such as 43-passage) successive cultivation using DEC showed a superior ability of immunization against MD. Whilst, the vaccine obtained by few passages successive cultivation using DEC followed by about 20 or more-passage successive cultivation, also showed a superior activity of immunization against MD as similar to that obtained on high passage successive cultivation using QEC alone. Thus, it has been statistically proved that MD virus is substantially made avirulent by successive cultivation using DEC and/or QEC and the resulting cultures are useful as MD vaccine.

EXAMPLE 3

A 7 to 12-day-old quail embryo was decapitated, amputated and viscerated, and then minced. 0.2% aqueous solution of trypsin was added thereto, followed by treatment according to the ordinary procedure to disperse the cells thereof. The obtained dispersion was subjected to a low speed centrifugalization to remove the aqueous phase, and then suspended in Earle's solution (containing 5% calf serum, 0.5% hydrolyzed lactalbumin and 50 mcg./ml. of erythromycin) in a concentration of 1.0 – 1.5 × $10^6$ cells per ml.

The thus obtained suspension was poured, by 100 ml., into Roux's bottles each having a capacity of 1000 ml. They were allowed to stand in an incubator at 37° C. for 2 days. Whereupon the abovementioned culture solution was removed, and the cells attached to the bottle wall were washed with Hanks' solution to remove the calf serum content. Then, the fibroblast culture in Roux's bottle was inoculated with 1 ml. of measles virus-infected suspension [TANABE strain of measles virus (name of the strain measles attenuated by successive cultivation using chorio-allantoic membrane of chick embryonated egg)]. Whereupon, 100 ml. of Eagle's culture solution were added thereto, and then cultivation was further conducted at 36° C. for 4 to 6 days. Upon termination of cultivation, the virus suspension was taken, and purified through centrifugalization or filtration to completely remove the culture cells. The infectivity of this virus suspension (measured by using FL cells) was $10^{4.0} - 10^{5.0} TCID_{50/ml}$ ($TCID_{50}$m infectivity of 50% cultivated tissue culture) and was sufficient to prepare dry measles vaccine.

On the other hand, the above-mentioned virus was subjected to 10-passage successive cultivation. At each passage of the successive cultivation, there was a virus suspension having an approximately equivalent and constant infectivity.

The adaptability of the thus obtained virus suspensions was examined in the same manner as described in Example 1. Then, the suspension was formulated to commercial measles live vaccines.

EXAMPLE 4

Quail embryo was treated in the same manner as described in Example 3, to obtain a tissue culture, and then inoculated with the aforementioned TANABE strain of measles virus followed by successive cultivation. To the virus suspension obtained at the 10th passage of successive cultivation were added stabilizers of 3% of arginine, 5% of succharose and 10% of hydrolyzed gelatin. The resulting suspension was poured, by a given volume, to small reservoirs and then freeze-dried. Upon long storage of the obtained formulations, the change in infectivity of each formulation was examined. The infectivity was $10^{4.3}$$TCID_{50/ml.}$ immediately after drying, and was changed extremely slightly even after stored at 4° C. for 12 months to $10^{4.2}$$TCID_{50/ml.}$ Accordingly, the maintenance of infectivity can be said to be very excellent. This fact suggests that the present vaccine formulations are very stable with respect to its immunizing activity and can be stored for a long time.

REFERENCE EXAMPLE 4

TANABE strain of measles virus (which had been highly attenuated by successive cultivation using chorio-allantoic membrane of chick embryonated egg) was subjected to 1-passage successive cultivation and 10-passage successive cultivation to obtain two kinds of virus suspensions, from which two kinds of vaccines were formulated. The comparison was made on these two kinds of vaccines and a vaccine (CAM-vaccine) prepared from viruses harvested from the chorio-allantoic membrane of chick embryonated egg which had been inoculated with the above-mentioned TANABE strain of measles virus.

The thus obtained CAM-vaccine was examined with regard to its adaptability as vaccine in the same manner as described in Example 1. The qualified vaccine was inoculated to a little child (8-month-to 3-year-old) having therein no measles antibody. The results are summarized in Table 5.

Table 5

| Derivation of vaccine | Infectivity/ Inoculation amount ($log_{10}$ $TCID_{50}$) | Number of inoculated children | Number of children showing increase in neutral antibody | Number of children showing rise in body temperature to more than 39° C. | Number of children showing eruption |
|---|---|---|---|---|---|
| Tissue culture of quail embryo fibroblast 1-passage cultivation | 3.7 | 5 | 5 | 0 | 0 |
| Tissue culture of quail embryo fibroblast 10-passage successive cultivation | 3.5 | 7 | 7 | 1 | 0 |
| Control* (CAM-vaccine) | 3.4 | 12 | 12 | 2 | 1 |

Note:
*Report at the general meeting of Society for Study of Measles vaccines in 1969, entitled "Results of inoculation with highly avirulent measles vaccines"Report by shigeharu Ueda at the 16th general meeting of Society for Research of Virus in 1969, entitled "Study on measles vaccines"

As clearly understood from Table 5, the two kinds of vaccines prepared employing a tissue culture quail embryo fibroblast have not a significant difference in clinical reaction from the CAM-vaccine, which is an original strain of the above-mentioned two kinds of vaccines, derived from chorio-allantoic membrane of quail embryonated egg, and showed a sufficient immunizing activity.

EXAMPLE 5

Quail embryonated eggs were inoculated with measles virus and influenza virus, respectively. The obtained vaccines were compared with the vaccines prepared by inoculation of chick embryonated egg with measles virus. The results are shown in Table 6.

Table 6

| Name of virus | | Measles [1] | | | | Influenza [2] | |
|---|---|---|---|---|---|---|---|
| Cultivation time | | 2 | 3 | 4 | 5 | 1 | 2 |
| Infectivity | Quail | 4.2 | 5.0 | 5.3 | 5.6 | 6.0 | 8.5 |
| | Chick | 4.0 | 4.7 | 5.5 | 5.5 | 6.5 | 8.5 |

Notes:
[1] $log_{10}TCID_{50/ml.}$
[2] $log_{10}EID_{50/ml.}$

The above table was obtained on the basis of the experiments as follows.

With regard to the preparation of measles vaccine, 0.1 ml. of amniotic sac of a 7-day-old embryonated egg was inoculated with the suspension of the aforementioned TANABE strain, and then cultivated at 35° C. for 5 days. With regard to the preparation of influenza virus, $A_2$ strain of influenza virus was inoculated to chorio-allantoic sac of a 8-day-old embryonated egg, and then cultivated at 37° C. for 5 days. At given intervals, the viruses were taken, formulated to virus suspens, and examined with regard to infectivity. The yield of virus obtained by employing a quail embryonated egg was as good as that obtained by employing a chick embryonated egg.

EXAMPLE 6

In the similar manner to that described in Examples 3 to 5, quail embryonated eggs and tissue cultures of quail embryo fibroblasts were inoculated with various kinds of viruses. The growth and propagation of virus were measured by known assays. The results are shown in Table 7.

As understood from Table 7, a quail embryonated egg and a tissue culture of quail embryo fibroblast are a superior culture medium for the adaptation thereto and propagation therein of various viruses. In addition, as described, a quail embryonated egg and a tissue culture of quail embryo fibroblast are scarcely subject to induction thereto of unfavorable factors, particularly chicken leukemia virus, and useful for produce high quality virus disease live vaccines.

Table 7

| Virus | Quail embryonated egg | Tissue culture of quail embryo fibroblast | Tissue culture of chick embryo fibroblast | Tissue culture of monkey kidney | Assay |
|---|---|---|---|---|---|
| Rubella | 3.5 | 3.5 | 4.0 | 4.5 | Tissue culture of African green monkey kidney ($\log_{10}I_nD_{50/ml.}$) |
| Mumpus | 8.0 | 8.2 | 8.0 | 7.8 | Tissue culture of chick embryo fibroblast ($\log_{10}TCID_{50/ml.}$) |
| Influenza A$_2$ | 8.5 | 7.2 | 7.5 | 7.5 | Chick embryonated egg ($\log_{10}EID_{50/ml.}$) |
| Influenza B | 8.0 | 7.5 | 7.2 | 6.0 | |
| Distemp- | 4.3 | 4.0 | 3.8 | 5.0 | Tissue culture of chick embryo fibroblast ($\log_{10}PFU/ml.$) |
| Vaccinia | 8.0 | 7.0 | 6.5 | — | Chick embryonated egg ($\log_{10}POFU/ml.$) |
| New castle | 8.0 | 8.0 | 8.2 | — | Chick embryonated egg ($\log_{10}InD_{50/ml.}$) |
| Japanese encephalitis | 7.8 | 8.5 | 7.5 | 8.5 | Tissue culture of chick embryo fibroblast ($\log_{10}PFU/ml.$) |
| Dengue fever | 4.5 | 5.0 | 4.5 | 5.0 | Mouse ($\log_{10}LD_{50/ml.}$) |
| Rabies | 7.3 | 4.0 | 3.8 | — | Mouse ($\log_{10}LD_{50/ml.}$) |
| Marek's disease | 3.5 | 4.8 | 4.1 | — | Tissue culture of duck embryo fibroblast ($\log_{10}PFU/ml.$) |

What is claimed is:

1. In a process for the production of a live virus vaccine by the tissue culture method comprising the adaptation, attenuation and propagation of a virus selected from the group consisting of rubella, mumps, influenza A, influenza B, distemper, Newcastle disease, Japanese encephalitis, dengue fever, rabies, and turkey Herpes viruses, the improvement comprising a. incubating the virus in a culture of a quail embryonated egg or tissue culture of a quail embryo fibroblast, and
 b. subjecting the virus to successive cultivation in a culture medium for a sufficient number of passages to propagate the virus, at least one passage in the successive cultivation being effected in a culture medium containing a quail embryonated egg or a quail embryo fibroblast.

2. A process according to claim 1, wherein said virus is a rubella virus.

3. A process according to claim 1, wherein said virus is a mumps virus.

4. A process according to claim 1, wherein said virus is an influenza A virus.

5. A process according to claim 1, wherein said virus is an influenza B virus.

6. A process according to claim 1, wherein said virus is a distemper virus.

7. A process according to claim 1, wherein said virus is a Newcastle disease virus.

8. A process according to claim 1, wherein said virus is a Japanese encephalitis virus.

9. A process according to claim 1, wherein said virus is a dengue fever virus.

10. A process according to claim 1, wherein said virus is a rabies virus.

* * * * *